United States Patent [19]

Cogan

[11] Patent Number: 5,755,759
[45] Date of Patent: May 26, 1998

[54] BIOMEDICAL DEVICE WITH A PROTECTIVE OVERLAYER

[75] Inventor: Stuart F. Cogan, Sudbury, Mass.

[73] Assignee: EIC Laboratories, Inc., Norwood, Mass.

[21] Appl. No.: 616,125

[22] Filed: Mar. 14, 1996

[51] Int. Cl.[6] ........................................ A61N 1/05
[52] U.S. Cl. ........................................ 607/116
[58] Field of Search ........................ 128/635, 637, 128/634, 642; 604/891.1, 892.1, 266; 607/1, 42, 45, 48, 49, 56, 57, 115, 116, 117, 118, 121, 137; 204/192.23

[56] References Cited

U.S. PATENT DOCUMENTS

| | | | |
|---|---|---|---|
| 4,647,472 | 3/1987 | Hiraki et al. | 427/39 |
| 4,853,251 | 8/1989 | Ishihara et al. | 427/38 |
| 5,133,594 | 7/1992 | Haas et al. | 359/275 |
| 5,238,866 | 8/1993 | Bolz et al. | 437/100 |
| 5,405,373 | 4/1995 | Petersson et al. | 607/121 |
| 5,530,581 | 6/1996 | Cogan | 359/265 |

FOREIGN PATENT DOCUMENTS 0144055  6/1985  European Pat. Off. ........ 204/192.23

OTHER PUBLICATIONS

Chang et al., "Novel Passivation Dielectrics—The Boron- or Phosphorus-Doped Hydrogenated Amorphous Silicon Carbide Films," J. Electrochem. Soc., 132, 418–422 (1985).

Primary Examiner—William E. Kamm

[57] ABSTRACT

A biomedical device provided with a protective overlayer with high electronic resistivity and low permeability to $H_2O$; the protective overlayer comprising at least one thin film of amorphous silicon oxycarbide (a-SiOC:H) in which the oxygen/carbon ratio is such that the electronic resistivity of the a-SiOC:H is greater than $10^{14}$ $\Omega$-cm and the $H_2O$ permeability is less than $5\times10^{14}$ molecules/sec-cm$^2$.

14 Claims, 10 Drawing Sheets

BIOMEDICAL DEVICE WITH A PROTECTIVE OVERLAYER

This invention was made with Government support under Contract No. N44-NS-2-2311 awarded by the National Institutes of Health. The Government has certain rights to this invention.

FIELD OF THE INVENTION

This invention relates to biomedical devices and, more particularly, to thin film materials and coatings used as dielectric, protective overlayers on biomedical devices.

BACKGROUND OF THE INVENTION

Surgical implants and, in particular, implantable electrodes and microelectronic devices that provide an electrical interface to the human nervous system are being developed for many applications. The electrodes may be implanted in the brain for cortical recording and stimulation, around major nerves for respiratory pacing and control of epilepsy, or in muscle to provide motor function in paralyzed individuals. The microelectronic devices, of which silicon microprobes are a typical example, are fabricated as planar structures with an array of electrode sites and integrated circuit elements on a single piece of Si that is chemically etched into a structure suitable for implantation. Applications of the microprobes include stimulation of the auditory system, regeneration of peripheral nerve, and intracortical recording and stimulation. Other emerging applications of microfabricated Si-based devices include micromechanical components such as pumps for implanted drug delivery systems and in vivo chemical sensors.

For stimulation applications, the electrical field associated with the transport of charge across the electrode-tissue interface at the electrode charge injection sites is responsible for eliciting the desired neural or muscular response. In neural recording, electrical signals associated with nerve activity are measured at the exposed electrode sites. A more detailed description of electrodes in peripheral nerve applications can be found in "Overview of Peripheral Nerve Electrode Design and Implantation," by Mortimer et al in *Neural Prostheses: Fundamental Studies*, edited by Agnew and McCreery. A description of the fabrication and applications of silicon microprobes is found in the scientific literature (for example, Anderson et al, IEEE Trans on Biomed. Eng. vol 36, p. 693, 1989; Kovacs et al, IEEE Trans. Biomed. Eng. vol 41, p. 567, 1994).

Common to these electrodes and implanted devices is the need to provide electrical insulation that protects the electrodes and microprobes from degradation in the physiological environment. For metal electrodes, prior art insulation is generally a polymer such as poly(fluorinated ethylene propylene) or a silicone elastomer. On microprobes prior art insulation is typically silicon dioxide and silicon nitride, deposited by low pressure chemical vapor deposition (LPCVD) or plasma enhanced chemical vapor deposition (PECVD). Migration of $H_2O$ and ions through the insulation used to protect the electrodes or microprobes is expected to cause corrosion or internal shorting of circuit elements. Microprobes with active electronics may operate at voltages of ±10 V, and both field assisted diffusion and imposed EMF effects are expected to exacerbate or initiate degradation processes associated with transport of $H_2O$ through the insulation.

Polymer coatings can exhibit low $H_2O$ and ion permeabilities but are often poorly adherent to metal and integrated circuit substrates. The poor adhesion leads to leakage of physiological electrolyte between the coating and substrate. This leakage can cause undesirable changes in electrochemical behavior of the electrode during charge injection. A further disadvantage of the polymer overlayers is the physical size they added to the implantable device. The polymer coatings range in thickness from a few micrometers (µm) to more than 20 µm. Microprobes and intracortical metal electrodes, in particular, have maximum cross-sectional dimensions that are often less than 80 µm. The additional thickness of the polymer overlayer contributes to trauma during implantation of the electrode, particularly when the implantation site is in the cortex, spinal cord, or within peripheral nerve.

The use of silicon oxide and silicon nitride as dielectric passivation for implantable integrated circuit devices has been described in the scientific literature (see for example, Hetke, et al, IEEE Tran Biomed. Eng. vol. 41, p. 314, 1994). However, as shown herein by example, Si oxide and nitride passivation have either inadequate $H_2O$ barrier properties or poor stability in physiological electrolytes and will, therefore, be limited in usefulness for implanted devices. The passivation is also deposited at elevated temperatures, >350° C., which may not be tolerated by all devices. In prior art, the use of amorphous silicon carbide (a-SiC:H) as a protective overlayer for integrated circuit elements has been taught by Hiraki et al (U.S. Pat. No. 4,647,472, March 1987) and Bolz et al (U.S. Pat. No. 5,238,866, August 1993). Both teach the use of the PECVD process using silane and methane as reactive gases. Bolz et al further teach the addition of phosphine ($PH_3$) to the reactive gas mixture to increase the electronic conductivity of the a-SiC:H for improved compatibility with blood. Hiraki et al also teach the addition of impurities of hydrogen nitrogen, oxygen and a halogen (e.g. Cl of F) for the purpose of maintaining low base-collector leakage currents in semiconductor devices. The impurity content of the a-SiC:H being preferably less than 10% of the stoichiometric composition of the compound formed between the impurity element and silicon. Although a-SiC:H has excellent properties as a $H_2O$ barrier, as will be shown herein by example, it exhibits undesirable electronic conductivity that limits its usefulness as an electronically insulating overlayer.

The essential properties of an electrically insulating, protective overlayer material for implantable devices are 1) stability in the physiological environment, and 2) a high electronic resistivity. The present invention is intended to overcome the deficiencies of prior art approaches to protecting implanted electrical devices by providing a means of protecting biomedical devices from ingress of $H_2O$ and ions for periods of time appropriate to chronic implantation. Applications of the devices include, but are not limited to, stimulation and recording in the cortex, spinal cord, peripheral nerve, and muscle. Non-electrical, implantable devices are also an appropriate application for the protective overlayer material of the present invention.

SUMMARY OF THE INVENTION

The present invention provides an implantable biomedical device with an electronically insulating protective overlayer that is substantially impervious to the transport of $H_2O$ and ions. The protective overlayer comprises one or more layers of thin-film materials, at least one of which is amorphous silicon oxycarbide (a-SiOC:H). The ratio of oxygen to carbon in the a-SiOC:H is chosen to provide a high electronic resistivity while maintaining low $H_2O$ and ion permeability.

DESCRIPTION OF THE PREFERRED EMBODIMENTS

Figure 1:
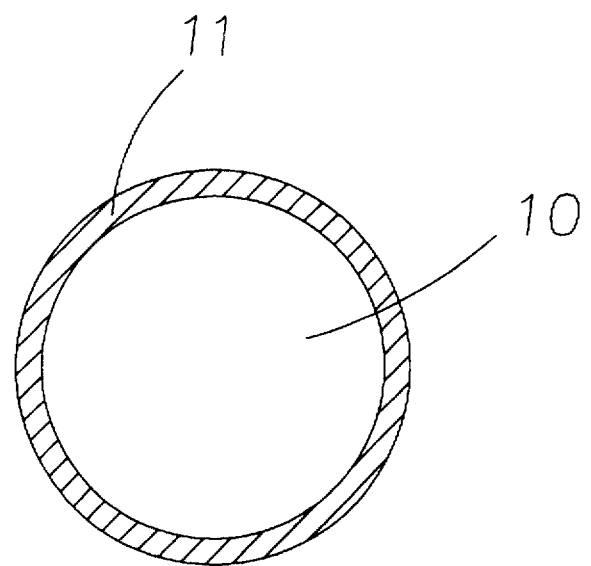
FIG. 1 is a cross-sectional, diagrammatic view of a metal electrode in a preferred embodiment of the present invention in which a thin film of a-SiOC:H is used as dielectric insulation.

Referring to FIG. 1, a cross-sectional view of a single-strand wire electrode is shown in a preferred embodiment of the present invention. Preferred materials for the wire (10) include Pt, Ir, PtIr alloys, Au, W, stainless steel, and other metals or alloys useful in recording or stimulation of physiological function. The outer layer (11) of FIG. 1 is the electronically insulating, protective overlayer of the present invention which contains one or more films, at least one of which is a-SiOC:H. An a-SiOC:H film thickness of 0.5 μm or less is sufficient to provide a useful level of protection from $H_2O$ and ion interactions with the wire electrode. The preferred maximum thickness of the a-SiOC:H is therefore about 5 μm while the preferred minimum thickness is about 0.05 μm.

Figure 2:
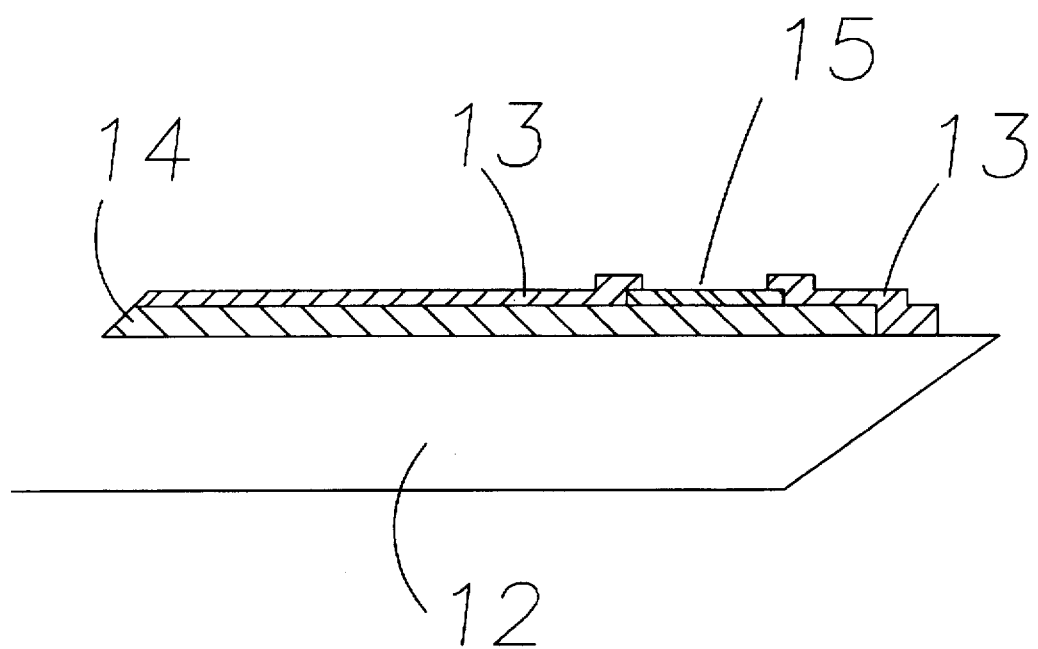
FIG. 2 is a cross-sectional, diagrammatic view of a charge injection site on a planar implantable device in a preferred embodiment of the present invention in which a thin film of a-SiOC:H is used as dielectric insulation.

In another embodiment of the present invention, shown in FIG. 2, a planar, implantable device is coated with the electronically insulating protective overlayer (13) containing one or more films, at least one of which is a-SiOC:H. The cross-section revealed by FIG. 2 is taken at a charge injection site (15) of the device and shows a Si substrate (12) and a conductive metal trace (14). For planar, integrated circuit devices the preferred thickness of the a-SiOC:H film is about 1 μm or less.

In a further embodiment of the invention, the a-SiOC:H film is combined with other dielectric films for improved barrier properties. For example, multilayer protective overlayers comprised of a-SiOC:H and a-SiC:H deposited on electrical devices have the advantage of high electronic resistivity, imparted by the a-SiOC:H, and exceptional stability, imparted by the a-SiC:H. When using a multilayer a-SiOC:H/a-SiC:H coating on an electrical device, the a-SiOC:H would typically be deposited between the active circuit elements and the a-SiC:H to preserve the advantage of high electronic resistivity. Prior art dielectrics such as LPCVD or PECVD Si oxide and Si nitride, as well as hard carbon (a-C:H), phosphosilicate glass (PSG), and other passivation materials can also be combined with a-SiOC:H in multilayer protective overlayers.

Another embodiment of the invention combines a-SiOC:H films with metallic films in a protective overlayer. The metallic films are useful for electrical shielding and grounding, or may be useful for modifying the biocompatibility of the implanted device. Preferred materials for the metallic films include Au, Pt, Ti, Ta, Ir, $PtSi_2$ and TiN.

Figure 3:
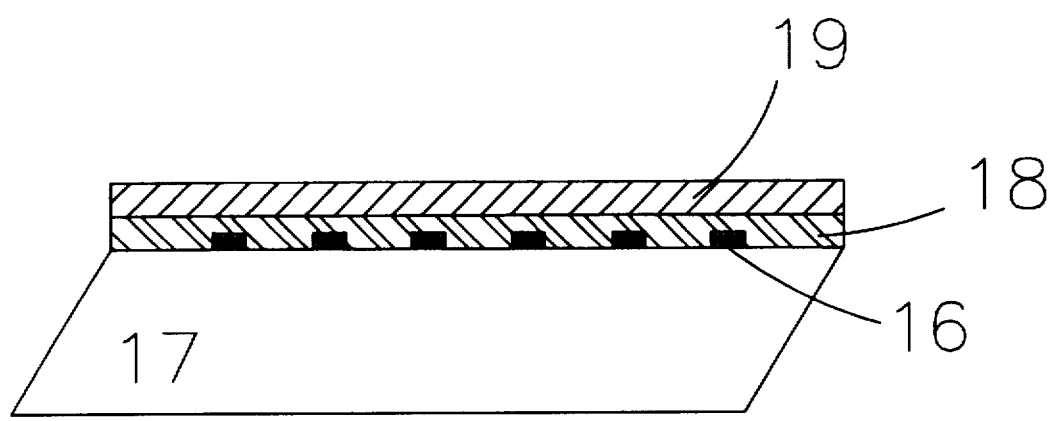
FIG. 3 is a cross-sectional, diagrammatic view of a planar implantable device in a preferred embodiment of the present invention in which a planarization layer is disposed between the device and the a-SiOC:H dielectric insulation for the purpose of preserving a-SiOC:H coating integrity as it traverses steps on the underlying substrate.

In an embodiment of the invention particularly useful for coating irregular surfaces, the a-SiOC:H film is combined with a planarization layer such as a spin-on-glass (SOG). The SOG smoothes out surface irregularities and provides a step-free surface over which the a-SiOC:H can be deposited. This embodiment is shown in FIG. 3 which reveals a cross-section of a Si-microprobe having electrically conducting traces (16) arrayed on a Si substrate (17). The SOG planarization layer (18) forms a smooth surface over which a coating of a-SiOC:H (19) has been deposited. A a-SiOC:H/SiC:H or other multilayer coating containing a-SiOC:H could also be deposited over the SOG. Other planarization materials and coating processes are well-known to those skilled in the development of dielectric passivation for integrated circuits and are not detailed herein.

A preferred method of forming a-SiOC:H films is PECVD from silane ($SiH_4$) and methane ($CH_4$) gas mixtures to which an oxidizer such as oxygen or nitrous oxide ($N_2O$) is added. The general PECVD process is well known to artisans of vacuum coating technology and is only briefly described herein. The PECVD apparatus comprises a vacuum pumped chamber containing two planar electrodes which are typically 1–3 cm apart. The biomedical device is placed on one of the electrodes which is usually heated with a resistive element embedded in the electrode. The other electrode is connected to a high frequency power supply that will typically operate at a frequency between 50 kHz and 13.56 MHz. Power supplies operating at microwave frequencies with electron cyclotron resonance (ECR) deposition systems may also be used. The reactive gas mixture is introduced into the chamber at a well-controlled flow rate and the gas pressure controlled by modulating the flow rate or by the use of a variable-sized orifice between the chamber and vacuum pumps. When the power supply is energized, a plasma of the reactive gas constituents forms between the electrodes causing an a-SiOC:H film to deposit on the surface of the biomedical device. Typical PECVD conditions used to produce a-SiOC:H overlayers of the present invention are listed in Table 1. Another preferred method of depositing a-SiOC:H films is reactive sputtering from a Si target using a gas mixture that includes methane with oxygen or nitrous oxide.

Prior art films of a-SiC:H deposited by the PECVD process exhibit an electronic resistivity of $10^{13}$–$10^{14}$ Ω-cm. Although this resistivity is high, it may still lead to undesirable electrical shorting between elements on an integrated circuit. In addition, for a ~0.5 μm thick dielectric overlayer, typical of that used to coat an integrated circuit device, a 10

V bias will lead to a steady state current of 20 nA/cm² across the overlayer-tissue interface. This current drain reduces the useful lifetime of batteries in implantable devices and may be deleterious to the tissue. The a-SiC:H taught by Bolz et al has an electrical resistivity of $10^4$ Ω-cm or less and is thus seen to be inappropriate as a dielectric protective overlayer. The a-SiOC:H of the present invention, as shown in Example 2, has an electronic resistivity of greater than $10^{14}$ Ω-cm.

The high electronic resistivity of a-SiOC:H is due, at least in part, to an increase in band gap energy associated with an increase in the oxygen to carbon ratio in the film. The oxygen:carbon ratio is controlled by the oxidizer/hydrocarbon ratio (e.g. $O_2/CH_4$ or $N_2O/CH_4$) used during deposition, higher ratios producing films with higher oxygen contents. An $O_2/CH_4$ or $N_2O/CH_4$ ratio of 1:8 is sufficient to produce a-SiOC:H films of high resistivity.

At higher oxidizer/hydrocarbon ratios, the carbon content of the a-SiOC:H is reduced and a film with properties similar to $SiO_2$ is produced. Although $SiO_2$ films are highly resistive, they have poor hermetic properties as shown by the leakage current measurements described in Example 1. At a bias of −5 V, the leakage currents are on the order of $1^{-5}$ A/cm², many orders of magnitude higher than those observed with a-SiOC:H.

The a-SiOC:H films of the present invention are distinguished from prior art protective overlayer materials by having a desirable combination of high electronic resistivity and stability in physiological electrolytes. The dissolution rate of a-SiOC:H in phosphate buffered saline is compared with those of prior art LPCVD $SiO_2$ and $Si_3N_4$ films in Table 2. The dissolution rate of a-SiOC:H is much less than 0.2 nm/day while LPCVD $SiO_2$ and $Si_3N_4$ films dissolve at 0.8 nm/day and 0.4 nm/day respectively. The manner in which the dissolution rates were measured is described in Example 5.

Following the convention used in prior art (Bolz et al, U.S. Pat. No. 5,238,866), the chemical formula for the amorphous silicon oxycarbide of the present invention is written as a-SiOC:H (a=amorphous). A chemical composition for the a-SiOC:H films has not been specified since the PECVD and sputtering processes can produce films that have a wide compositional range that still embody the essential features of the present invention. For example, when $N_2O$ is used as a source of oxygen or when $N_2$ is used as a diluent gas for $SiH_4$, some nitrogen is incorporated into the a-SiOC:H. Since the chemical reactions in the PECVD process are incomplete at low deposition temperatures, some hydrogen (H) is incorporated into the films. The H originates from the source materials such as $SiH_4$, tetraethylorthosilicate (TEOS), $CH_4$, and other hydrocarbons and volatile Si-containing compounds. The formula a-SiOC:H is not meant to indicate a specific oxygen/carbon ratio, nor H or N content. The a-SiOC:H films of the present invention are differentiated from prior art a-SiC:H and other dielectrics such as LPCVD $SiO_2$ and $Si_3N_4$, by having a combination of 1) a high electronic resistivity which is greater than $10^{14}$ Ω-cm, 2) a $H_2O$ permeability of less than $5 \times 10^{14}$ molecules/sec-cm² and 3) low solubility in physiological electrolytes.

EXAMPLE 1

Figure 4:
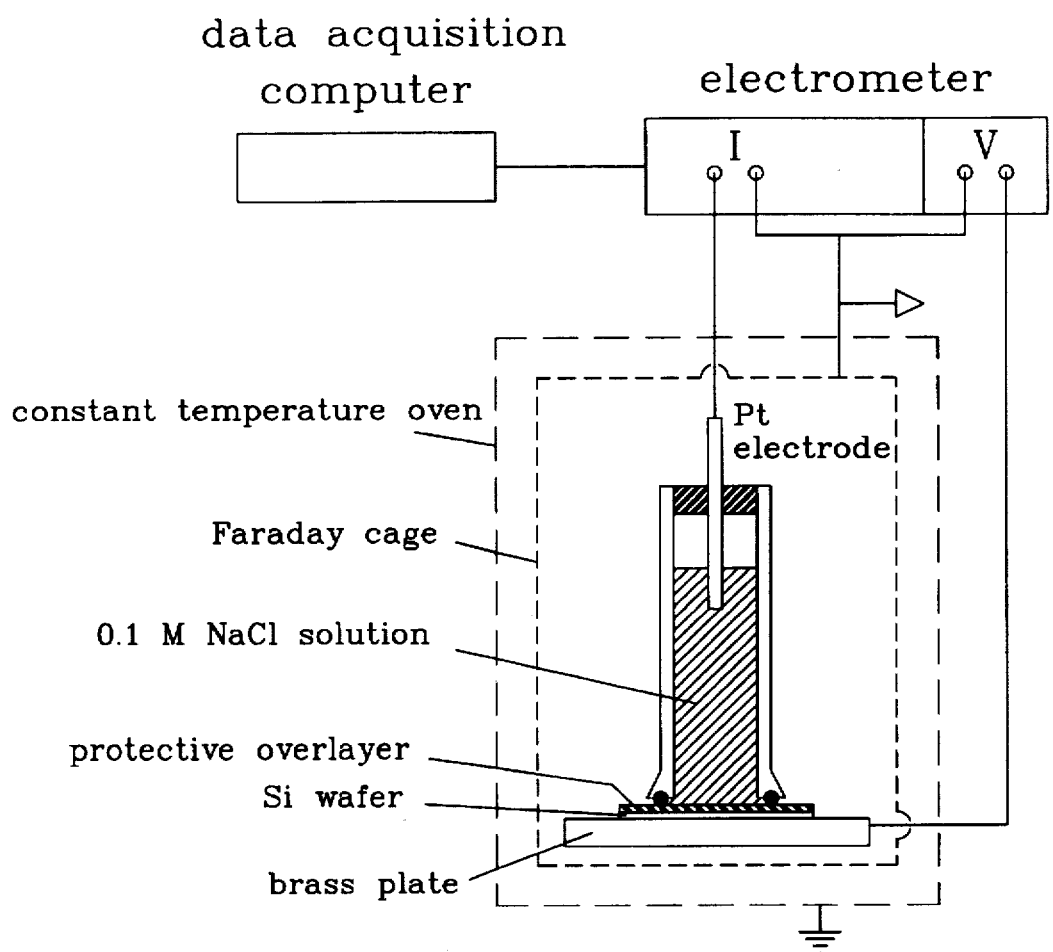
FIG. 4 is a diagrammatic view of the experimental setup used to measure leakage currents through protective overlayer materials.

To illustrate the advantageous properties of a-SiOC:H as a protective overlayer for biomedical devices, the rate of $H_2O$ and ion transport through a-SiOC:H films was determined using leakage current measurements. The use of leakage current measurements for evaluating dielectric passivation on biomedical devices has been described in the scientific literature by Hetke et al, op cit . An a-SiOC:H film was deposited onto a thermally oxidized Si wafer at a substrate temperature of 400° C. using deposition conditions described in Table 1. The a-SiOC:H film thickness was about 0.5 μm. A portion of the a-SiOC:H film was placed in contact with an aqueous electrolyte of composition 0.8% NaCl buffered with monobasic and dibasic sodium phosphate to a pH of 7.4. A platinum electrode was placed in the electrolyte and an external power supply used to apply a voltage between the Pt electrode and Si substrate. The current flowing between the Pt electrode and the coated Si wafer was measured as a function of the applied voltage. The resulting steady-state DC current at each voltage level was related to the rate at which $H_2O$ is transported through the a-SiOC:H to the Si/$SiO_2$ interface. At this interface the $H_2O$ is either reduced or oxidized, depending on the magnitude and polarity of the applied voltage bias, giving rise to the faradaic current measured in the external circuit. FIG. 4 shows the experimental arrangement used to make the leakage current measurements. When protective overlayer materials with good $H_2O$ barrier properties are evaluated using the leakage current measurement, the magnitude of the currents is extremely small, often less than $10^{-13}$ A per square centimeter of film area. For this reason, great care in the design of the experimental arrangement and choice of measurement equipment must be made.

Figure 5:
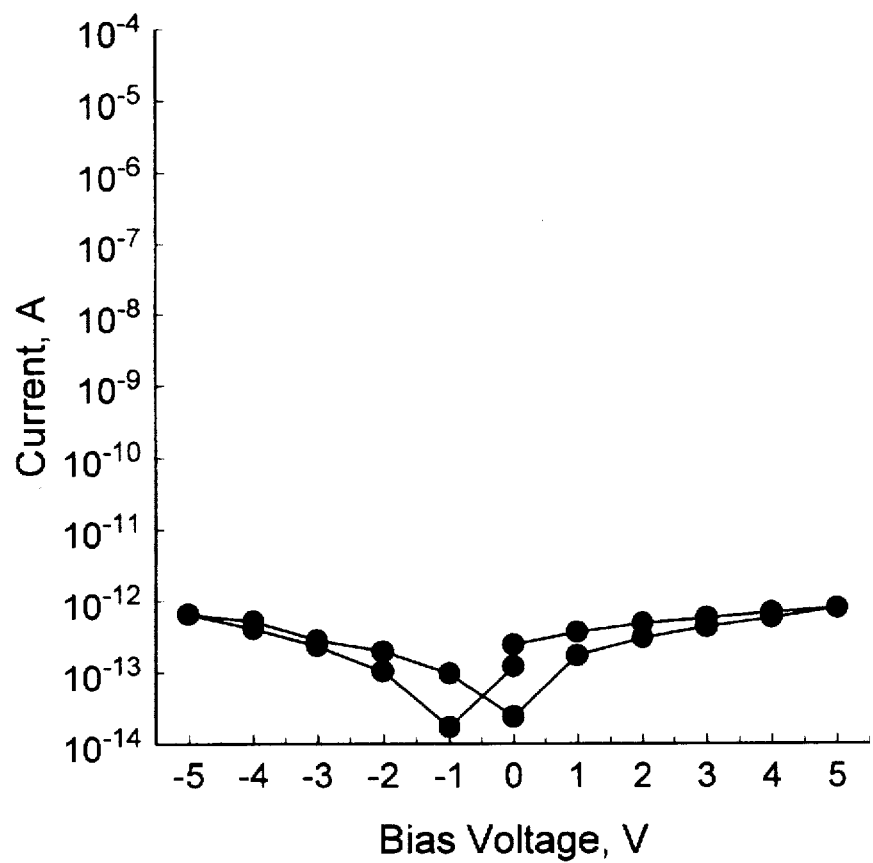
FIG. 5 shows leakage currents measured through an a-SiOC:H film deposited at a substrate temperature of 400° C.
Figure 6:
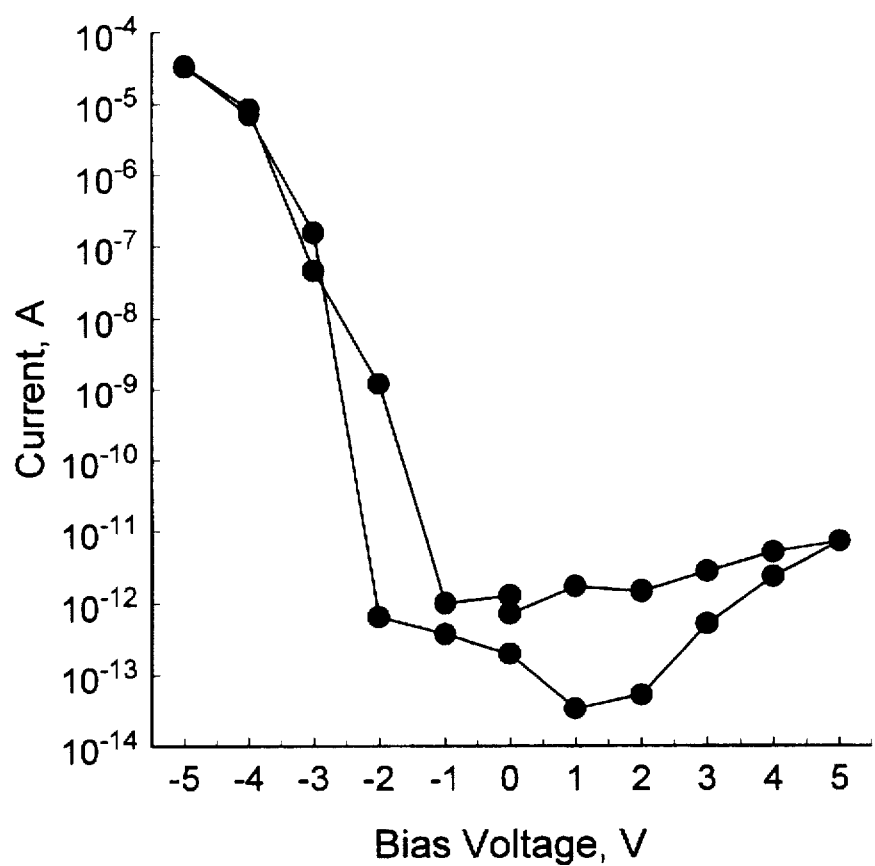
FIG. 6 shows leakage currents through a prior art LPCVD $SiO_2$ film deposited at a temperature of 900° C.

An example of the leakage currents measured through a PECVD a-SiOC:H film subjected to a voltage bias of ±5 V is shown in FIG. 5. The absolute value of the current is used in FIG. 5 and subsequent leakage current figures to allow use of a logarithmic scale. At a bias of −5 V volts the maximum current observed was $7 \times 10^{-13}$ A. For comparison, the leakage current response of LPCVD $SiO_2$, a protective overlayer material used in prior art coatings, is shown in FIG. 6. At −5 V, the leakage through the $SiO_2$ is ~$5 \times 10^{-5}$ A, about 8 orders of magnitude greater than that observed with a-SiOC:H.

An estimate of the transport rate of $H_2O$ through the protective overlayers was obtained from the leakage current measurements. The leakage currents at the −5 V bias are due to reduction of $H_2O$ at the Si/$SiO_2$ interface in accordance with the reaction $$H_2O + e^- \geq OH^- + \tfrac{1}{2}H_2$$

Since the reaction requires one $H_2O$ molecule per electron, the leakage current per unit area can be used to calculate a $H_2O$ transport rate using

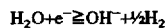

$$R_{H_2O} = \tfrac{j}{F} \cdot N_0$$

where $R_{H_2O}$ is the rate of $H_2O$ transport (molecules/sec-cm²), j the leakage current density (A/cm²), F Faraday's constant (96,300 Coulombs/equivalent) and $N_o$ is Avogadro's number ($6.02 \times 10^{23}$ molecules/equivalent). The rate of $H_2O$ transport through the a-SiOC:H is $7 \times 10^6$ molecules/sec-cm². For the prior art $SiO_2$ protective overlayer the leakage currents, shown in FIG. 6, indicate a $H_2O$ transport rate of $5 \times 10^{14}$ molecules/sec-cm².

EXAMPLE 2

The electronic resistivities of a-SiOC:H and a-SiC:H were determined from the slope of the current-voltage response of films deposited by PECVD on glass coated with a film of tin-doped indium oxide (ITO). The ITO is used an electrical back contact. Front electrical contact pads of Au were deposited on the a-SiOC:H and a-SiC:H films and the current flow through the thickness of the films measured in response to a voltage applied between the ITO and the Au pads. The calculated resistivity of the a-SiC:H was $3 \times 10^{13}$ $\Omega$-cm. The a-SiOC:H was too resistive for an accurate measurement and a lower bound of $10^{16}$ $\Omega$-cm was estimated from the current-voltage data. The electronic resistivity of a-SiOC:H is comparable with $SiO_2$ or $Si_3N_4$ dielectric coatings used in conventional integrated circuit passivation while the a-SiC:H is more conductive.

EXAMPLE 3 OF THE PRIOR ART

Figure 7:
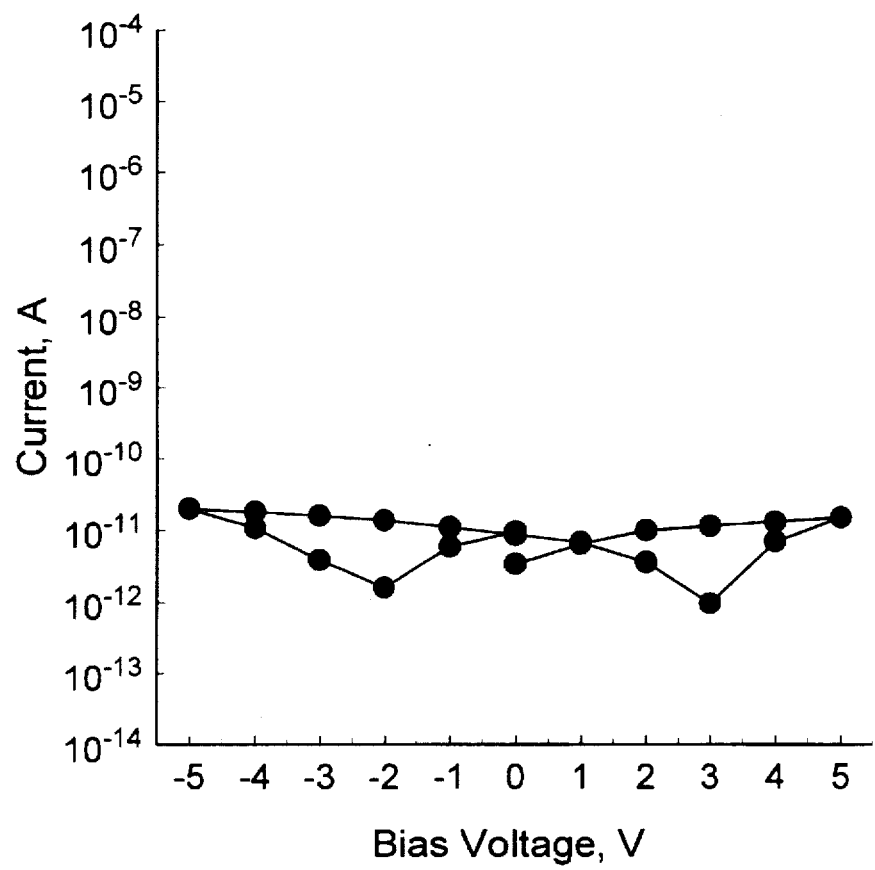
FIG. 7 shows leakage currents measured through a prior art a-SiC:H film deposited at a substrate temperature of 400° C.

Example 3 is provided as an illustration of the undesirable leakage currents that may be encountered with prior art a-SiC:H coatings. A prior art protective overlayer material of a-SiC:H was deposited at a substrate temperature of 400° C. by PECVD using $SiH_4$ and $CH_4$ reactive gases. The a-SiC:H film thickness was 0.5 µm. The leakage currents measured through the a-SiC:H are shown in FIG. 7. The leakage current measured through the a-SiC:H film is $2 \times 10^{-11}$ $A/cm^2$ at $-5$ V, a factor of ~30 higher than observed with a-SiOC:H films of the same thickness. The higher leakage currents through the a-SiC:H are associated with electron conduction to the electrolyte/a-SiC:H interface rather than diffusion of $H_2O$ or ions through the a-SiC:H.

EXAMPLE 4

Figure 8:
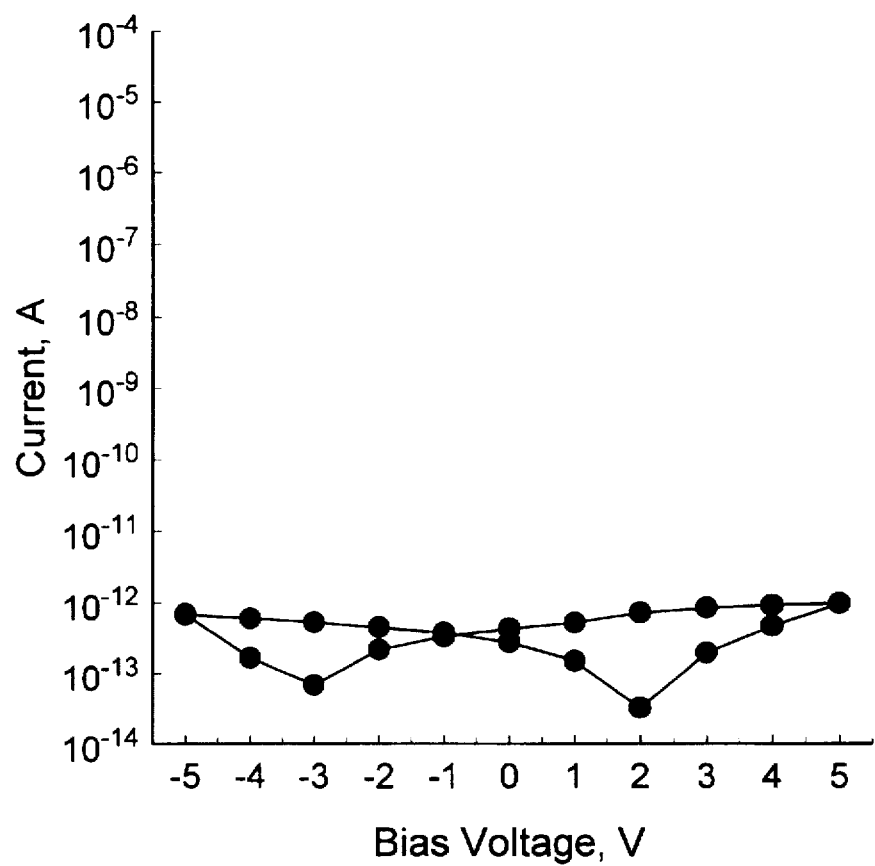
FIG. 8 shows leakage currents measured through an a-SiOC:H film of the present invention deposited at a substrate temperature of 100° C.

Example 4 is provided to illustrate the low leakage currents obtained with a-SiOC:H films of the present invention deposited by PECVD at a low substrate temperature. An 0.5 µm thick a-SiOC:H films was deposited on a thermally oxidized Si wafer at a substrate temperature of 100° C. using a reactive gas plasma of $SiH_4$, $CH_4$, and $N_2O$. Leakage currents were measured through the a-SiOC:H film using the method described in Example 1. The leakage currents, shown in FIG. 8, were similar to those obtained with a-SiOC:H deposited at a 400° C. substrate temperature and less than the prior art films of a-SiC:H films described in Example 3.

EXAMPLE 5

Figure 9:
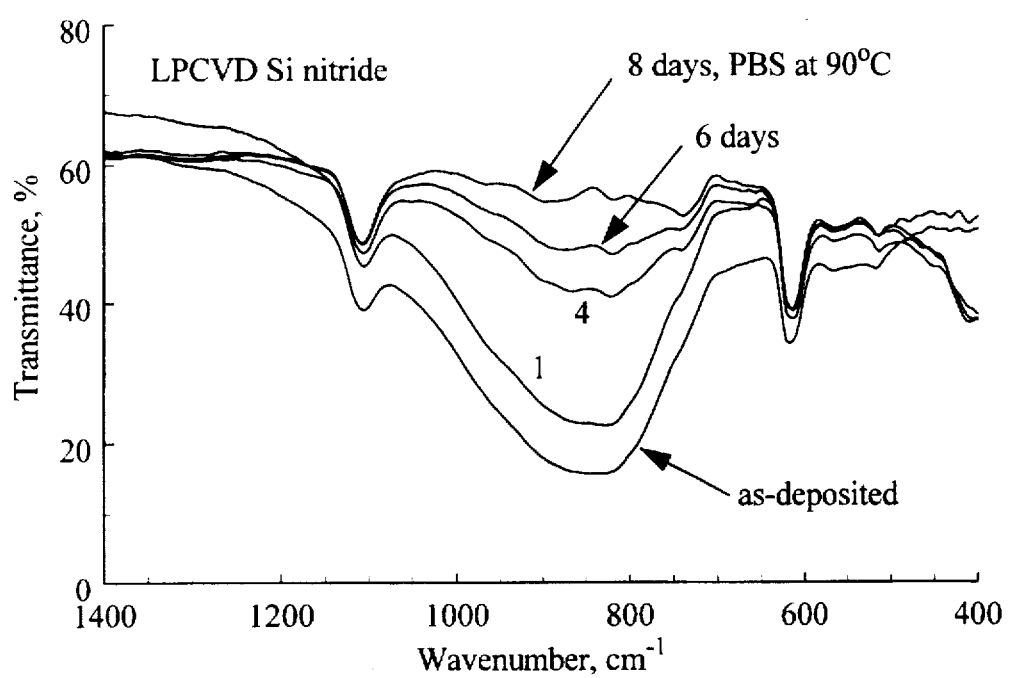
FIG. 9 is a series of infrared transmittance spectra showing the reduction in intensity of the Si—N stretching band in a prior art film of LPCVD $Si_3N_4$ soaked in a physiological electrolyte at 90° C.
Figure 10:
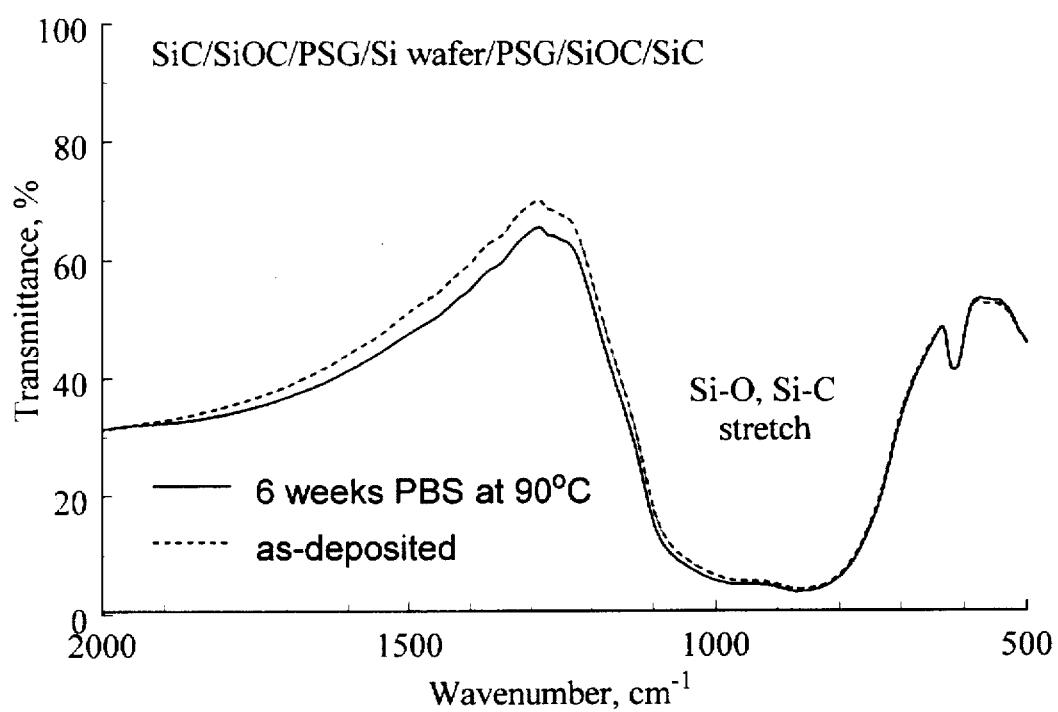
FIG. 10 shows infrared transmittance spectra of a protective overlayer of the present invention soaked in a physiological electrolyte at 90° C.

The stability of PECVD a-SiOC:H, a-SiC:H, and low pressure chemical vapor deposited (LPCVD) films of $SiO_2$ and $Si_3N_4$ were evaluated by accelerated soak tests in phosphate buffered saline (PBS) at 90° C. The dielectric films were deposited on both sides of polished Si wafers. The PECVD a-SiOC:H and a-SiC:H films were deposited at a substrate temperature of 400° C. or less while the LPCVD $SiO_2$ and $Si_3N_4$ films were deposited at substrate temperatures greater than 800° C. using materials and processes well known to skilled artisans. Dissolution rates were calculated from changes in the intensity of infrared absorption bands. The reduction in intensity of the Si—N stretching band at ~800 $cm^{-1}$ in a 400 nm thick prior art film of LPCVD $Si_3N_4$ is shown in FIG. 9. After 8 days in PBS, the LPCVD $Si_3N_4$ film had entirely dissolved from the Si substrate. A protective overlayer in a preferred embodiment of the present invention incorporating a spin-on-glass planarization layer and an a-SiOC:H/a-SiC:H bilayer was soaked for 6 weeks in PBS at 90° C. The infrared absorption spectra over the 6 week soak period are shown in FIG. 10. There was no reduction in intensity of the stretching bands from 800–1100 $cm^{-1}$, indicating no dissolution of the a-SiOC:H/a-SiC:H protective overlayer. A compilation of dissolution rates for prior art dielectrics and the a-SiOC:H of the present invention, soaked in PBS at 37° C., is provided in Table 2. The a-SiOC:H film has a low dissolution rate and, as demonstrated in Example 2, has an advantageously high electronic resistivity. This example serves to demonstrate the improvement in stability obtained with the protective overlayer material of the present invention compared with prior art materials.

TABLE 1

| process pressure | 20 to 950 millitorr |
|---|---|
| process gases and flow rates: | |
| silane | 1 to 500 sccm |
| methane | 1 to 500 sccm |
| nitrous oxide or oxygen | 1 to 500 sccm |
| substrate temperature | 100° C. to 500° C. |

TABLE 2

| LPCVD Si nitride | 0.4 nm/day |
|---|---|
| LPCVD Si oxide | 0.8 nm/day |
| PECVD Si carbide | <0.2 nm/day |
| PECVD Si oxycarbide | <0.2 nm/day |

What is claimed is:

1. An improved biomedical device comprising;
   A biomedical device having at least one surface to be disposed upon use to living tissue;
   A protective overlayer disposed over said surface of said biomedical device;
   Said protective overlayer comprising at least one thin-film of a-SiOC:H having an oxygen to carbon ratio such that the electronic resistivity of said a-SiOC:H is $10^{14}$ $\Omega$-cm and the water transport rate through a 0.5 µm thick film of said a-SiOC:H is less than $5 \times 10^{14}$ molecules/sec-$cm^2$.

2. The biomedical device of claim 1, wherein said protective overlayer is comprised of at least one thin-film of a-SiOC:H containing nitrogen as an impurity, the concentration of said nitrogen being less than the amount necessary to increase the dissolution rate of said a-SiOC:H to 0.4 nm/day or greater in a physiological electrolyte at 90° C.

3. The biomedical device of claim 1, wherein said protective overlayer further comprises at least one thin-film planarization layer being disposed between said implantable biomedical device and said a-SiOC:H thin-film.

4. The biomedical device of claim 1, wherein said protective overlayer further comprises at least one film of a-SiC:H, said a-SiC:H having an electronic resistivity of $10^{14}$ $\Omega$-cm or less.

5. The biomedical device of claim 1, wherein said protective overlayer further comprises at least one films chosen from the group of dielectric materials consisting of Si oxide, Si nitrid, hard carbon, and phosphosilicate glass.

6. The biomedical device of claim 1, wherein said protective overlayer comprises at least one conductive film made from metal chosen from the group of metallic materials consisting of Ti, Ta, Au, Pt, Ir, Pt, $PtSi_2$ and TiN and alloys thereof.

7. The biomedical device of claim 6 wherein said conductive film is made from Ti.

8. The biomedical device of claim 6 wherein said conductive film is made from Ta.

9. The biomedical device of claim 6 wherein said conductive film is made from Au.

10. The biomedical device of claim 6 wherein said conductive film is made from Pt.

11. The biomedical device of claim 6 wherein said conductive film is made from Ir.

12. The biomedical device of claim 6 wherein said conductive film is made from $PtSi_2$.

13. The biomedical device of claim 6 wherein said conductive film is made from TiN.

14. The biomedical device of claim 1, wherein said protective overlayer comprises at least one thin-film of said a-SiOC:H and at least one conductive film.

* * * * *